US00PP12187P2

(12) United States Plant Patent
Spivey

(10) Patent No.: US PP12,187 P2
(45) Date of Patent: Nov. 6, 2001

(54) PHOTINIA PLANT NAMED 'COLWILLOW'

(75) Inventor: James W. Spivey, Devine, TX (US)

(73) Assignee: Color Spot Nurseries, Inc., San Antonio, TX (US)

( * ) Notice: Subject to any disclaimer, the term of this patent is extended or adjusted under 35 U.S.C. 154(b) by 0 days.

(21) Appl. No.: 09/519,865

(22) Filed: Mar. 6, 2000

(51) Int. Cl.[7] ..... A01H 5/00

(52) U.S. Cl. ..... Plt./226

(58) Field of Search ..... Plt./226

*Primary Examiner*—Bruce R. Campell
*Assistant Examiner*—Anne Marie Grüberg
(74) *Attorney, Agent, or Firm*—C. A. Whealy

(57) ABSTRACT

A new and distinct cultivar of Photinia plant named 'Colwillow', characterized by its compact and outwardly spreading plant habit; small narrow leaves; attractive foliage color; and freely branching habit.

2 Drawing Sheets

BACKGROUND OF THE INVENTION

The present Invention relates to a new and distinct cultivar of Photinia plant, botanically known as *Photoinia×fraseri*, and hereinafter referred to by the cultivar name Colwillow.

The new Photinia is a product of a planned breeding program conducted by the Inventor in San Antonio, Tex. The objective of the breeding program was to develop new compact Photinia cultivars with dark and attractively colored foliage.

The new Photinia originated from a self-pollination of an unidentified selection of *Photinia×fraseri*. The cultivar Colwillow was discovered and selected by the Inventor as a single plant within a population of 10,000 progeny in a controlled environment in San Antonio, Tex., in 1994. The selection of this plant was based on its compact plant habit, small narrow leaves, and attractive foliage colors.

Plants of the new Photinia differ from plants of the parent, the unidentified selection of *Photinia×fraseri*, in the following characteristics:

1. Plants of the new Photinia are more compact and more outwardly spreading than plants of the parent selection.

2. Plants of the new Photinia have smaller and much narrower leaves than plants of the parent selection.

3. Plants of the new Photinia and the parent selection differ in leaf coloration.

Asexual reproduction of the new cultivar by terminal cuttings taken at San Antonio, Tex., has shown that the unique features of this new Photinia are stable and reproduced true to type in successive generations of asexual reproduction.

SUMMARY OF THE INVENTION

The following traits have been repeatedly observed and are determined to be the unique characteristics of 'Colwillow'. These characteristics in combination distinguish 'Colwillow' as a new and distinct cultivar:

1. Compact and outwardly spreading plant habit.
2. Small narrow leaves.
3. Attractive foliage color.
4. Freely branching habit.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Photinia.

The photograph on the first sheet comprises a top perspective view of a typical plant of 'Colwillow'.

The photograph on the second sheet comprises a close-up view of typical leaves of 'Colwillow'.

DETAILED BOTANICAL DESCRIPTION

Plants of the cultivar Colwillow have not been observed under all possible environmental conditions. The phenotype may vary somewhat with variations in environment such as temperature and light intensity, without, however, any variance in genotype. The following observations, measurements and comparisons describe plants grown in San Antonio and Keller, Tex., under outdoor conditions which closely approximate commercial production conditions. Plants used for the descriptions were grown in 25-cm containers and were about one year old.

In the following description, color references are made to The Royal Horticultural Society Colour Chart except where general terms of ordinary dictionary significance are used.

Botanical classification: *Photinia×fraseri* cultivar Colwillow.

Parentage: Self-pollination of unidentified selection of *Photinia×fraseri.*

Propagation:

*Type cutting.*—Terminal cuttings.

*Time to initiate roots.*—Summer: About 60 to 90 days at 32° C. Winter: About 90 to 120 days at 16° C.

*Time to produce a rooted cutting or liner.*—Summer: About 120 days at 32° C. Winter: About 160 days at 16° C.

*Rooting habit.*—Numerous, fine to thick; freely branching.

Plant description:

*General appearance/growth habit.*—Perennial evergreen shrub; compact, upright and outwardly spreading.

*Branching habit.*—Responds well to pruning; freely branching; lateral branches potentially forming at every node after removal of terminal apex.

*Plant height.*—About 38 cm.

*Plant width.*—About 47 cm.

*Lateral branch description.*—Diameter: About 1.2 cm. Internode length: About 1.4 cm. Color: Woody: Close to 197A to 197B. Young: Close to 187A. Texture: Young stems, pubescent: woody stems with lenticels. Lenticles: Length: About 1 mm. Shape: Oval. Density: Numerous, closely and randomly spaced. Color: Close to 199C to 199D.

*Foliage description.*—Leaves simple, alternate; generally symmetrical; abundant, densely foliated. Length: About 7.5 cm. Width: About 1.6 cm. Shape: Linear. Apex: Sharply acute. Base: Cuneate to attenuate. Margin: Sharply serrate. Texture: Leathery, tough, very durable; upper surface, glabrous; lower surface of young leaves, sparsely pubescent. Color: Young foliage, upper surface: Glossy, close to 166A with slight reddish, close to 187A, overtones. Young foliage, lower surface: Close to 184A. Fully expanded foliage, upper surface: Glossy, 147A. Fully expanded foliage, lower surface: Close to 146A. Petiole: Length: About 7.5 mm. Diameter: About 1.5 mm. Color: Upper surface: 147A. Lower surface: 146C. Base: 187A.

Flower description: Flowers have not been observed.

Disease resistance: Plants of the new Photinia have demonstrated good resistance to pathogens common to Photinia.

Seed development: Seed production has not been observed.

It is claimed:

1. A new and distinct cultivar of Photinia plant named 'Colwillow', as illustrated and described.

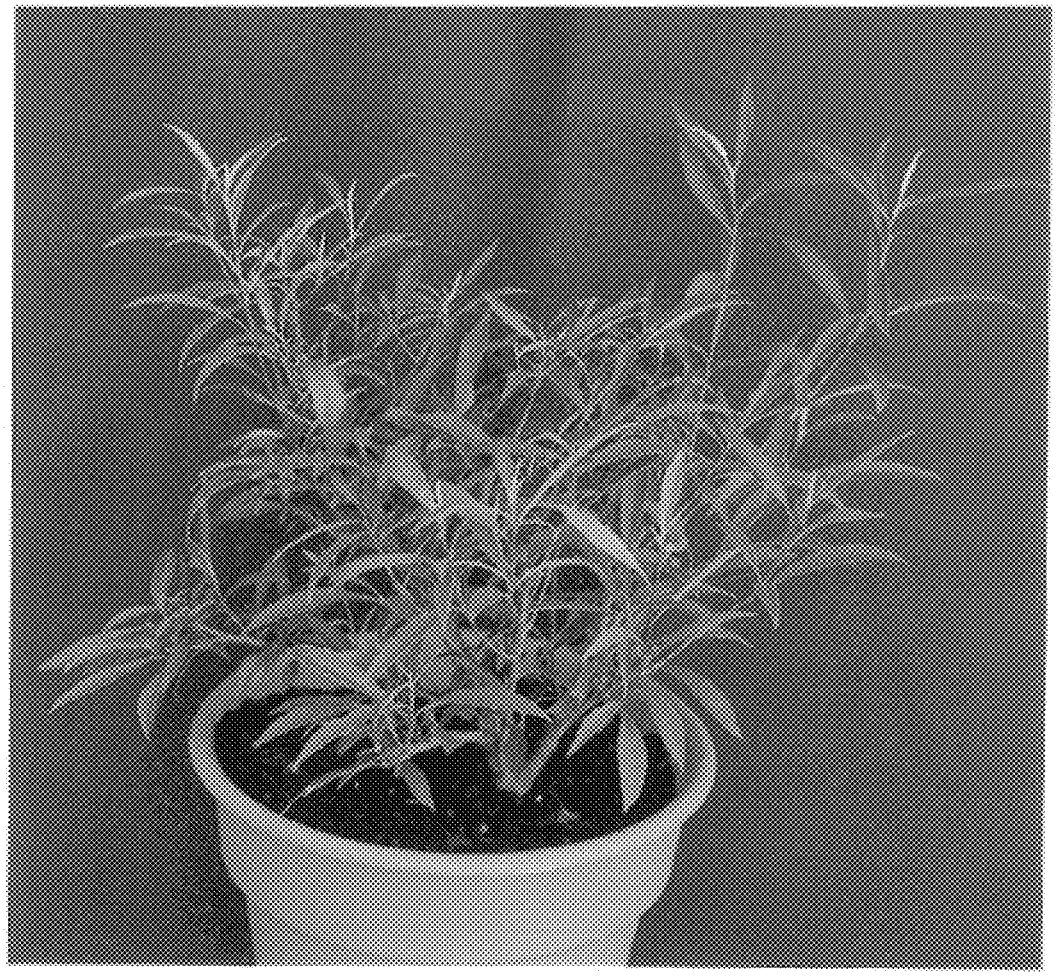

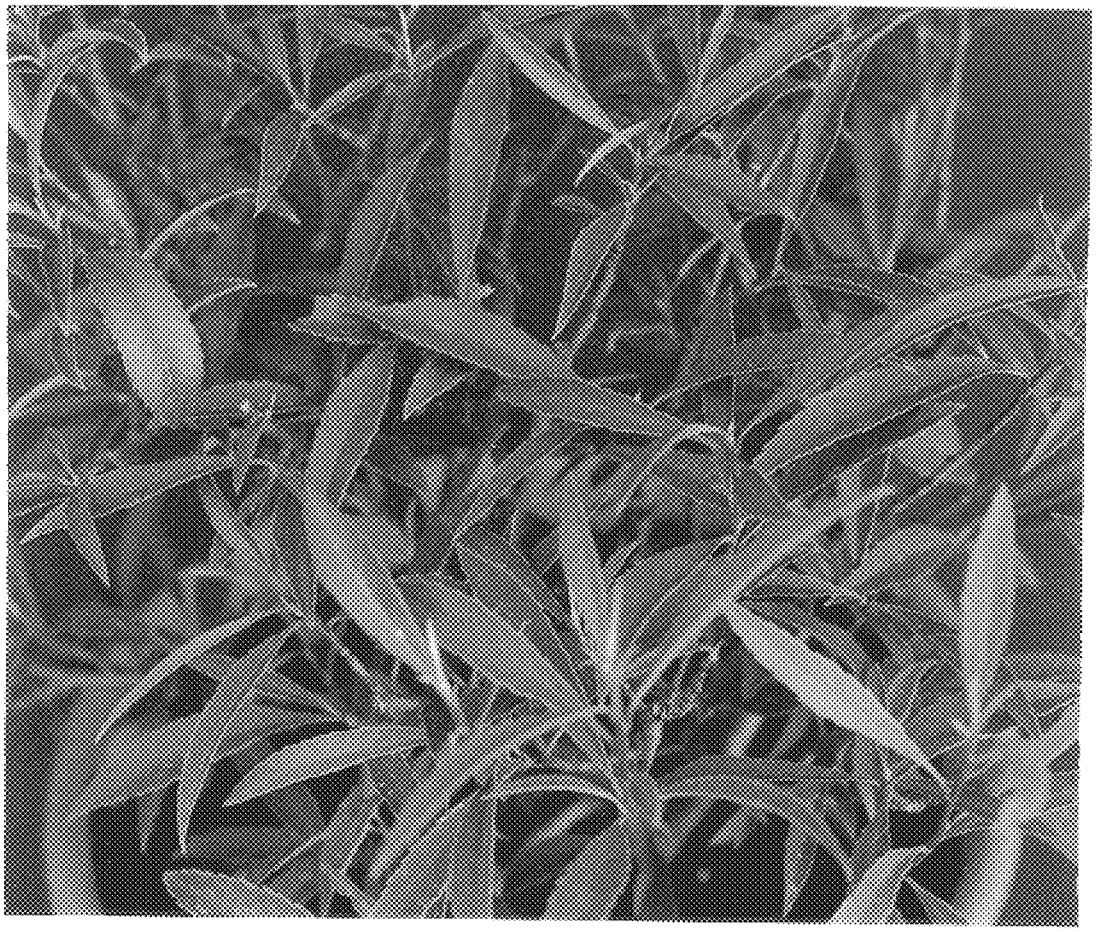

* * * * *